United States Patent [19]

Noll et al.

[11] Patent Number: 5,725,875
[45] Date of Patent: *Mar. 10, 1998

[54] PROTECTIVE SKIN COMPOSITION

[75] Inventors: Charles R. Noll; Virginia M. Noll, both of Pulaski, Wis.

[73] Assignee: Microbarriers, Pulaski, Wis.

[*] Notice: The term of this patent shall not extend beyond the expiration date of Pat. No. 5,370,876.

[21] Appl. No.: 448,549

[22] PCT Filed: Jan. 10, 1994

[86] PCT No.: PCT/US94/00304

§ 371 Date: Jan. 2, 1996

§ 102(e) Date: Jan. 2, 1996

[87] PCT Pub. No.: WO94/15461

PCT Pub. Date: Jul. 21, 1994

[51] Int. Cl.$^6$ .................... A61L 15/00; A01N 25/24
[52] U.S. Cl. .................... 424/445; 424/407; 424/7.1; 424/9; 514/50; 514/718; 514/157; 514/938
[58] Field of Search .................... 424/407, 445, 424/7.1, 9; 514/50, 718, 157, 938

[56] References Cited

U.S. PATENT DOCUMENTS

| | | |
|---|---|---|
| 2,698,824 | 1/1955 | Morgulis . |
| 3,890,264 | 6/1975 | Sidi et al. . |
| 3,929,705 | 12/1975 | Minieri . |
| 3,952,000 | 4/1976 | Sidi et al. . |
| 3,962,271 | 6/1976 | Sidi et al. . |
| 4,012,261 | 3/1977 | Sidi et al. . |
| 4,022,906 | 5/1977 | Sidi et al. . |
| 4,343,788 | 8/1982 | Mustacich . |
| 4,404,196 | 9/1983 | Dandt et al. . |
| 4,448,906 | 5/1984 | Deinet et al. . |
| 4,467,013 | 8/1984 | Baldwin . |
| 4,479,795 | 10/1984 | Mustacich . |
| 4,500,338 | 2/1985 | Young et al. . |
| 4,614,675 | 9/1986 | Ona et al. . |
| 4,671,957 | 6/1987 | Holtshousen . |
| 4,738,987 | 4/1988 | Mattson et al. . |
| 4,803,066 | 2/1989 | Edwards . |
| 5,019,604 | 5/1991 | Lemole . |
| 5,039,711 | 8/1991 | Blount . |
| 5,043,155 | 8/1991 | Puchalski et al. . |
| 5,126,136 | 6/1992 | Merat et al. . |
| 5,194,172 | 3/1993 | Taneri et al. . |

FOREIGN PATENT DOCUMENTS 9217184  10/1992  WIPO .

OTHER PUBLICATIONS

S. Budavari et al., The Merck Index (11th Ed.), 1989, pp. 51, 168, 715, 1055, 1151 and 1597.

Hoover et al., Remington's Pharmaceutical Sciences (15th Ed.), 1975, pp. 1224 and 1644–1645.

David H. Blount, Chemical Abstracts, Polyol–Alkali Metal Silicate Emulsion, vol. 98, No. 26, Abstract No. 216607z, US, A, 4,376,178 (1983).

Chemical Abstracts, vol. 116, No. 8, Issued 1991; Yamamoto et al, "Oil-in-Water Solid Cosmetic Emulsions", Abstract No. 66921w, JP03141211 (1991).

DiPiro et al., "Pharmacotherapy A Pathophysiologic Approach," Elsevier Science, New York, NY (1989), p. 1129.

Primary Examiner—Marianne M. Cintins
Assistant Examiner—M. Moezie
Attorney, Agent, or Firm—Birch, Stewart, Kolasch & Birch, LLP

[57] ABSTRACT

A protective cream composition contains 15 to 40 wt % of an alkali metal fatty acid salt having from 8 to 18 carbon atoms, an effective amount of a topical agent such as an antimicrobial compound, 5 to 20 wt. % of a polyol effective as an emollient, 0.5 to 8.0 wt. %, of an alkali metal silicate, and the balance water. Such a composition can be applied to the skin to protect health care workers and other from infection. The cream dries to form a topical barrier on the skin, and also contains an agent effective against, for instance, viruses such as human HIV. Once a medical operation is completed, the film formed from the dried cream can be washed off with soap and water. Other topical agents present in the composition include, for instance, suncreens, insect repellents and chemical repellents.

21 Claims, 2 Drawing Sheets

PROTECTIVE SKIN COMPOSITION

This application is a 371 of PCT/US94/00304 Jan. 10, 1994.

FIELD OF THE INVENTION

This invention relates to a protective composition, more particularly to a skin cream of the kind that forms a protective film on skin or other surfaces.

BACKGROUND OF THE INVENTION

Many known antimicrobial topical compositions are designed for treatment of existing wounds or skin disorders, and are not used as barriers to future infectious contact. These topical agents penetrate the wound or infected area, and deliver the antimicrobial compound to the site of the contamination. Many of these commercially available topical formulations consist of an oil based carrier such as petrolatum or liquid paraffin which is insoluble or nearly insoluble in water, plus a bioactive agent. Such compositions tend to be greasy, tacky, stain causing, and may be difficult to remove. Specific topical bioactive skin ointments used to treat infections are described, for example, in Edwards U.S. Pat. No. 4,803,066, issued Feb. 7, 1989, and Holtshousen U.S. Pat. No. 4,671,957, issued Jun. 9, 1987.

Other antimicrobial surface-coating compositions have been formulated for the coating of substrates such as wood, metal, textile, thread, canvas, carpeting, paper and masonry. Most of these compounds are long lasting, toxic, irritating to skin, and not easily removable. Many are formulated to provide a semi-permanent polymer coating. Ona et al. U.S. Pat. No. 4,614,675, issued Sep. 30, 1986, and Baldwin U.S. Pat. No. 4,467,013, issued Aug. 21, 1984, describe an antimicrobic used to treat fibers, fiber-containing material and non-woven fabrics. Mustachich et al. U.S. Pat. Nos. 4,479,795 and 4,343,788 describe a carboxylate antimicrobial agent releasably incorporated into permeable polymers. Young et al. U.S. Pat. No. 4,500,338, issued Feb. 19, 1985, discloses a hydrolyzable organic titanium compound containing a microbiocide and an optional organopolysiloxane for use as a surface disinfectant.

Other prior art has focused on the incorporation of an antimicrobial agent into surface coating substances such as paints or varnishes to prevent the decomposition of the surface coating. Deinet et al. U.S. Pat. No. 4,448,906, issued May 15, 1994, Dandt et al. U.S. Pat. No. 4,404,196, issued Sep. 13, 1983, Sidi et al. U.S. Pat. Nos. 4,022,906, issued May 10, 1977, 4,012,261, issued Mar. 15, 1977, 3,962,271, issued Jun. 8, 1976, 3,952,000, issued Apr. 20, 1976, 3,890, 264, issued Jun. 17, 1975, and Minieri U.S. Pat. No. 3,929, 705, issued Dec. 30, 1975 all describe such inventions.

In the field of protective hand creams, one composition marketed under the Invisible Glove trademark is made of about 60% water, 14% glycerin, 1% sodium silicate, and 25% soap (sodium laurate). This composition has been commercially successful as a cream applied prior to undertaking a task that involves exposing the hands to inks, grease, paints or the like. The cream dries to form a thin, slightly tacky film on the hands that repels contaminants. Mattson et al. U.S. Pat. No. 4,738,987 discloses a comparable skin care composition compounded as a dispersion of water with soap, a water-soluble alkali metal silicate, and sulfonated castor oil having a pH adjusted with acid to 6.5 to 10. See also Morgulis U.S. Pat. No. 2,698,824, issued Jan. 4, 1955, which describes a non-bioactive silicone-based ointment which provides a non water soluble protective layer on the skin.

These compositions tend to fall into one of several categories: compositions containing an antimicrobial designed for immediate use on the skin, compositions containing an antimicrobial and an agent such as a siloxane to provide extended substantivity on the skin, and compositions for temporary use (i.e., which wash off readily with soap and water) but which lack an antimicrobial. None are particularly suited for protecting health care workers. During surgery, doctors and health care workers are commonly exposed to the blood or other bodily fluids of the patient. Protective gowns, masks and gloves may not provide adequate protection of all exposed skin areas, and may hinder delicate operations. A need exists for a skin protectant composition that can be worn under of protective clothing and on skin which remains exposed, which composition minimizes the chance that a health care worker will contract AIDS, sexually transmitted disease, or other infectious diseases. However, the composition should be readily removable when a procedure or operation is over so that the physician or health care worker can wash it off and remove any residual contamination. The present invention addresses this need.

SUMMARY OF THE INVENTION

This invention provides a protective composition, particularly a skin cream, from formulations of an aqueous base, preferably an oil-in-water emulsion, containing a topical bioactive agent such as an antimicrobial agent. A preferred protective composition according to the invention contains, as basic ingredients, an alkali-metal fatty acid salt, a topical bioactive agent such as an antimicrobial agent, an alkali-metal silicate, and water. In particular, a preferred skin cream which provides a barrier from viruses, bacteria and other microorganisms consists essentially of 15 to 40 wt. % of an alkali metal fatty acid salt having from 8 to 18 carbon atoms, an effective amount, generally about 0.1 to 15.0 wt. %, of an antimicrobial compound, 0.5 to 8.0 wt. % of an alkali-metal silicate, up to 20 wt. % of a polyol effective as an emollient and/or viscosity adjusting agent, and the balance water. In each case, weight percent amounts are based on the weight of the total composition. Such a composition dries quickly on the skin and forms a film that repels liquids and also kills "germs" that might otherwise survive to eventually penetrate the barrier.

According to a further aspect of the invention, the foregoing composition is used in carrying out one or a series of surgeries or medical procedures. The subject applies the cream according to the invention to his or her skin in likely exposed areas, such as hands, face and upper body, puts on protective clothing, and performs the operation or procedure. After the operation is over, for example, the subject washes the film left by the cream off. If a further operation is scheduled, the cream can then be freshly reapplied without danger of residual contamination from the prior operation. These and other aspects of the invention are more fully described below.

The present invention is further directed to a protective skin composition wherein the antimicrobial agent is substituted by or used in combination with a topical bioactive agent such as a sunscreen, moisturizer, chemical repellant, insect repellant, and other topical pharmaceuticals and the like. All of these various active ingredients may be used alone or in combination with one another.

In another embodiment of the invention, the composition may be used as a barrier per se. Under these circumstances, the presence of a topical bioactive agent is not required.

DETAILED DESCRIPTION OF THE INVENTION

As discussed above, a need exists for a topical barrier containing, for instance, a microbiocide that provides protection by direct application to exposed skin and may be easily removed with water. The composition of the invention may be used as protection against microorganisms, viruses, insect bites, sun, poison ivy/oak, burns and other skin irritants. A composition for administration to the skin to form an adherent, continuous, flexible coat should serve two purposes: (1) it should form a barrier against infection, and (2) it should serve as an effective vehicle for one or more topical bioactive agents, such as antimicrobial agents that destroy infectious organisms that come in contact with the topical barrier. Such a composition could be used in place of gloves in some circumstances, or may be used to provide an extra measure of protection underneath gloves or on areas the gloves do not cover, such as the forearms, and would be of immense use to individuals such as health care workers, police, fire and rescue personnel, and anyone else who is at risk of exposure to infectious bodily fluids. This invention can be used in place of latex gloves or beneath gloves to help prevent allergic reactions to persons sensitive to latex or other rubber or synthetic rubber products, including patients and health care workers.

Ideally, a skin cream should be non-toxic, without side effects, non-irritating, non-greasy, non-tacky, odorless, easy to apply, easy to remove, and provide excellent protection from infection. It should provide an effective barrier for an extended time (for example, up to 4 hours, preferably up to 24 hours) or until removed. The present invention can provide these characteristics to a greater extent than many prior preparations.

The phrase "bioactive agent" refers to a compound which protects or otherwise benefits the skin of a human or animal when applied topically to the skin. The term "skin" refers to all human or animal external surfaces including the epidermis, mucous membranes, cornea, nails, teeth and hair. While many applications will be limited to the epidermis, nails and hair for toxicological reasons, applications for the other surfaces are contemplated.

Representative examples of various topical bioactive agents which may be used in the present invention include the following topical bioagents shown in Table 1. However, the invention is not limited to the topical bioagents listed below.

TABLE 1

Topical Agent

A. Antimicrobials

Phenol

HO—⌬

Cresol (o,m,p)

HO—⌬—Me

Hydroxy-Benzoates

HO—⌬—CO$_2$H

Resorcinol/4-hexylresorcinol

HO—⌬—(C$_6$H$_{13}$)
        |
        OH

Hexachlorophene

Triclosan

Salicylanilide

Tetracycline (Quinolones)

TABLE 1-continued

Topical Agent

Peptides and Derivatives:

Bacitracin,
Gramicidin,
Polymyxin B

Glycosidic:

Streptomycin B,
Neomycin A,
Erythromycin,
Gentamicin

Others:

Chlorhexidine

Thiols/Antidandruff pyrithione

Imidazoles/Antifungals miconazole

Topical Germicidals such as Acids/Surfactants

+ SLS

Mercurials such as thimersal

TABLE 1-continued

Topical Agent

Ureas such as triclocarban,
cloflucarban

Penicillins

Quaternary $$C_{18}H_3 - \overset{\oplus}{N} - (CH_3)_3$$
$$Cl^{\ominus}$$

B. Sunscreens

Benzoates

Oxybenzone (dioxy)

Cinnamic Acid Derivatives

C. Insect Repellents 1,3-Hexanediol

TABLE 1-continued

Topical Agent

Citronellal (structure shown)

Toluamide (structure shown, CON(Et)₂ on methylbenzene)

D. Humectants/Moisturizers

Polyols such as Glycerol,
Polyethylene glycol
Hyaluronic acid (structures shown)

E. Skin Protectants

Silicones (structure shown)

Perfluorocarbons (structure shown)

Allantoin (structure shown)

Methyl Silylates (structure shown)

F. Skin Penetration Enhancers

Caprolactams (structure shown)

Sulfoxides (structure shown)

G. Anti-Inflammatory Agents

Corticosteriods (structure shown)

Salicylates (structure shown)

H. Anti-Allergy Agents

Cromolyn (structure shown)

TABLE 1-continued

Topical Agent

Pentigitide
ASP — SER — ASP — PRO — ARG

I. Hair Growth Agents

Minoxidil

J. Skin Emollients

Alcohols
R — OH
Cetyl Alcohol
Glyceryl Hydroxystearate
PPG- and PEG- Monoesters

K. Antioxidants

Ascorbates

Gallates

Thiocompounds

HO—CH$_2$CH$_2$—S—CH$_2$CH$_2$—OH

L. Hair Conditioning Agents

Proteins and Amino Acids
R — OH
Hydroxylated Fats
Dihydroxyethyl- Amine Oxide (or Glycinate)

R—N—(O or CH$_2$CO$_2$H)
with CH$_2$CH$_2$OH groups

M. Coloring Agents

Phenols and Naphthols
Aminophenol
2-Naphthol
D&C Green No. 8

Hydroxy azo derivatives
D&C Red No. 9

TABLE 1-continued

Topical Agent

D&C Orange No. 4

N. Fragrances/Flavors

Phenols
Menthyl Salicylate
Thymol
Vanillin

Any compatible antimicrobial agent of the kind presently employed in cream/ointment formulations may be used in the topical antimicrobial composition of the invention. Suitable agents may possess antiviral, antibacterial and other activities. Preferred antimicrobial agents include those which have been shown to be effective against the HIV virus such as Nonoxynol-9 (nonylphenoxypolyethoxyethanol) and AZT (azidothymidine, or zidovudine). Nonoxynol-9 has also become well recognized as an effective virucide and of assistance in killing the AIDS virus. The U.S. surgeon general has urged the public to utilize condoms in combination with nonoxynol-9 to fight AIDS. Clinical 327 pg. 12, Nov. 23, 1983 FDA Regulation. Vaginal foam:12.5% nonoxynol-9 to vaginal jelly 2%. Effective for up to 24 hours for sponge at 1 g nonoxynol-9. Other useful antimicrobials include chlorhexidene, hexachlorophene (i.e. 0.5 to 4 w/v %), iodine (i.e. about 2 to 10% solution in water), sodium oxychlorosene (i.e. a complex of the sodium salt of dodecylbenzene-sulfonic acid and hypochlorous acid at about 0.1 to 0.4% solution in water), tetrachlorosalicylanilide (2% IMPREGNON), silver sulfadiazine (i.e. SSD-1%), butaconazole nitrate (i.e. 2%), chloroxylenol, and fungicidal agents such as triacetin (i.e. TINCTURE) and aluminum chlorhydrate. A preferred antimicrobial agent for this invention is Nonoxynol-9, because this agent has proven safe and effective for human use.

Sunscreening agents which may be used include aminobenzoates, benzophenones, and cinnamates (i.e. about 8%).

Other topical bioactive agents within the scope of the present invention include various AIDS related complex therapeutic agents, analgesics (i.e. acetaminophen), macrolides, about 2% erythromycin, parenterals (i.e. Polymyxin B-Bacltracin), sulfonamides, salicylates (i.e. triethanolamine salicylate 10%), topical analgesic, local and topical anesthetics (i.e. benzocaine 20%), glycolic acid (i.e. 5% to 10%), anorectal products (i.e. creams, foams, lotions, ointments (i.e. NUPERCAINAL)) and other materials such as aerosol sprays (i.e. HURRICANE topical anesthetic aerosol spray (20% Benzocaine) (Beutilich)), anthelmintics (i.e. permethrin 1 to 5%), antiarthritics (i.e. flurbiprofen), antibiotics (i.e. 2% mupirocin), active ingredients for herpes treatment such as those in Nerpacin-L Cold Sore Lip Balm (Campbell), Zovirax Ointment 5% (i.e. Acyclovir-9[2-hydroxyethoxylmethly)quanine] (Burroughs Wellcome), active ingredients for insect bites and stings such as those in Dermalde Aloe Cream (i.e. Aloe vera Jel) (Dermaide Research), Dermoplast Anesthetic Pain Relief Lotion and Spray (i.e. Benzocaine 8% and menthol 0.5%) (Whitehall), moisturizers (i.e. 10% urea), photosensitizers (i.e. 1% methoxsalen) such as those in Oxsoralen lotion 1% (ICN Pharmaceuticals), pruritus medications (i.e. about 0.06% fluoccinonide), psoriasis agents, scabicides (i.e. 1% lindane), seborrhea treatment (i.e. 0.5% coal tar, 2% salicyclic acid, 2% sulfur), antihistamines (i.e. Benadryl cream, 2% diphenhydramine), anti-inflammatory agents (i.e. about 0.5% alclometasone dipropionate), sulfonamides, cleansing agents (i.e. 7.5 to 10% povidone-indine), coal tar, dandruff medications, deodorants (i.e. aluminum chloride (hexahydrate) 20% w/v), dermatitis relief agents (i.e. nystatin-triamcinolone acetonide), detergents (i.e. Betadine Skin Cleanser containing povidone-iodine 7.5%), drying agents (i.e. Formaldehyde-10%), emollients, epidermal and cellular growth agents (i.e. vitamins A and E), fungicides (i.e. nystatin and triamcinolone acetonide), antiseptics (i.e. about 2 to 3.2% glutaraldehyde, about 0.25 to 5% sodium hypochlorite, thimerosal, about 0.25% triclosan, about 0.2 to 3% hexachlorophene, chlorhexidine gluconate, benzalkonium chloride), antiparasitics (i.e. lindane, the active ingredient in KWELL at 1%), antiglaucomatous agents (i.e. betaxolol HCl, $C_{18}H_{29}NO_3HCl$, the active ingredient in BEPTOPTIC, at 0.25% of base suspension), bee sting relief agents (i.e. benzocaine 8% and menthol 0.5%), disinfectants, sanitizers, germicides, bactericides, antiviral agents, algaecides, preservatives, chlorine compounds, iodine compounds, phenols, bisphenols, salicyanilides, carbanilides, amphoteric surfactants, mercurials, silver compound, etc. as listed in Physicians Desk Reference published by Medical Economics Data, 1992 edition and by publications of the EPA.

The concentration of antimicrobial/biocidal agent and other topical bioactive agents in the present invention will depend on the strength, for example, of the antimicrobial required. For example, usually only a small amount of the antimicrobial compound is needed. The addition of as little as 0.1% by weight of one or more of the topical bioactive agents including the antimicrobial agent will usually provide a measurable increase in protection. A range of 0.1 to 15 wt. % is preferred for the topical bioactive agent of the invention. With respect to the antimicrobial agent, excess amounts of the antimicrobial compound ordinarily do not provide further improvement in the properties of the surface-coating compositions and reduce the effectiveness of the skin barrier.

The precise amount of the topical bioactive agents such as the antimicrobial compound that will provide optimum protection for a given composition will depend on such factors as the activity of the particular topical compound employed, its toxicity, the propensity of the compound to cause irritation, the duration of use contemplated, the choice of materials which make up the cream base, and the application for which the coating compound is intended. Accordingly, the amount of the topical bioactive agent may vary widely, and combinations of several agents having different activities may be desirable.

The topical bioactive agent is preferably dispersed in an oil-in-water (o/w) emulsion base comprised of an alkali metal fatty acid salt such as sodium palmirate or sodium taurate, an alkalimetal silicate such as sodium or potassium silicate, in water. The water soluble salts of fatty acids, derived from alkaline hydrolysis (saponification) of plant or animal fats and oils which are widely used in cosmetic products, are used in the invention to provide water-repellency.

Alkali-metal salts of saturated or unsaturated fatty acids having from 8 to 18 carbon atoms are preferred. These include, by way of illustration only, sodium caprylate (C6), sodium laurate (C10), sodium myristate (C12), sodium palmirate (C14), sodium oleate (C16, 1 double bond), and sodium stearate (C16). The alkali metal salt of a fatty acid is generally one which is solid at room temperature so that it forms a solid film on the skin in combination with the silicate. The fatty acid salt component comprises between 15 and 40 wt. %, especially between 20–30 wt. % of the surface coating composition.

An alkali-metal silicate is added to the composition in an amount effective to reduce the tackiness of the fatty acid component and to enhance the effectiveness of the topical barrier. The amount of alkali metal silicate added is between about 0.5 to 8 wt. %, preferably from about 0.5 to 3 wt. %. The alkali-metal silicate may be sodium silicate ($Na_4SiO_4$), potassium silicate, or may comprise a siloxane oligomer or polymer such as polydimethylsiloxane, or salt thereof, having equivalent characteristics.

The composition of the invention should have a viscosity suitable for topical application. A polyol may be added no achieve and maintain the proper viscosity, as well as to prevent excessive drying and cracking of the surface film. Polyols such as glycerin also act as emollients. Preferred polyols include glycerin, sorbitol and propylene glycol. The polyol is preferably used in an amount of 5 to 20 wt. % of the composition. The composition of the invention may further contain other additives such as pigments, emulsifiers, supplemental biocides, and the like.

The composition of the invention may be used in a variety of applications. One embodiment of the product is in response to the need for secondary topical barriers that will help protect health care workers (i.e., nurses, doctors, technicians), public servants (i.e., E.M.T.'s, police, fire personnel), home health care providers, family members, or anyone needing protection from infectious contact with another person's bodily fluids. Thousands of people, ordinarily through occupational choice, must face contact with such infectious fluids, some of which carry fatal infections (i.e., the HIV or AIDS virus). The lethal quality of this infection has justifiably created significant concern and apprehension among all those involved in health care and has manifested itself in two ways. First, greater numbers of people are choosing not to pursue or continue careers that place them at risk. Fewer employees results in correspondingly poorer quality and quantity of health care and public service for both infected and non-infected persons. Second, the possibility of AIDS has created a perception that all those being treated have a potentially fatal infection unless proven otherwise.

For health care applications, the composition of the invention both coats the skin with a protective barrier that inhibits infection from entering the body through the skin, and kills infectious organism/viruses before they enter the body. The composition also coats and seals wounds with a protective barrier so as to prevent infection. Use of the composition in accordance with the method of the invention should provide a means of reducing the overall risk of infection and promote a more secure, less apprehensive attitude towards both infected and non-infected persons in health care workers.

An unexpected quality of the preferred composition of the invention, the skin cream described above, as is its propensity to coat small cuts, abrasions, or sores with a somewhat thicker layer of barrier, thus making the most accessible areas for infection the most protected. Bodily fluids of another coming in contact with the barrier tend to release the antimicrobial agent, e.g., nonylphenoxypolyethoxyethanol, allowing it to destroy infectious organisms such as HIV. The skin film/coating allows the health care worker to apply a secondary barrier to skin, particularly in areas of the body which cannot be gloved or clothed, such as the face. This coating further provides a secondary barrier when applied to areas of the body where clothing or gowns or gloves suffer failure or saturation, such as the chest, abdomen, upper arms, face and hands, the outcome being a less infectious health care environment.

In light of the foregoing, a method of protecting a person working in proximity to bodily fluids such as blood or urine from infection from such fluids includes the initial step of applying to the skin of such a worker a protective composition consisting essentially of an aqueous base composition as described above and the antimicrobial agent. The base composition dries in a short time to form a film on the skin effective as a topical barrier against bodily fluids, i.e., that substantially prevents the contaminating fluids from reaching the skin. In addition, the film contains the antimicrobial agent in an amount effective to kill one or more types of infectious organisms, and can be removed with soap and water.

The health care worker wears the film while performing a task such as a surgical operation or medical procedure in close proximity to a patient which may be the source of infected bodily fluids, particularly HIV infected blood. Some surgical operations or procedures, such as open heart surgery, routinely involve contact between the blood of the patient and the physician. Incidental contact between the doctor and the patient's blood is nearly unavoidable in such situations, and in this context the method of the invention is particularly valuable.

The surgeon, nurse, technician or other medical worker normally puts on protective garments such as scrub suit, surgical gloves, mask and the like. Such garments can be worn over skin to which the protective composition has been applied to provide additional protection. The protective composition may also be applied to areas of skin to which not covered by protective garments, such as the face and neck.

The protective film is removed from the worker's skin upon completion of the task. For this purpose, the film of the invention must be readily removable, preferably by washing it from the skin with soap and water, to remove any residual contamination. For this purpose, the protective composition is preferably the cream discussed above consisting essentially of 15 to 40 wt. % of the alkali-metal fatty acid salt having from 8 to 18 carbon atoms, an effective amount of the antimicrobial compound, 5 to 20 wt. % of a polyol effective as an emollient, 0.5 to 8.0 wt. %, of an alkali metal silicate, and the balance water. However, other compositions comprising a removable film-forming base and an antimicrobial agent can be used.

After the medical operation, procedure, or other comparable task is done and the film has been removed, the method of the invention can be repeated during the same day, or even immediately. This permits the health care worker to perform one or more additional medical operations or procedures without risk of contaminating one patient with infection from another due to residual film on the skin. Antimicrobial skin compositions according to the prior designed for long term use are generally not suitable for this purpose.

Other uses for the composition of the invention also exist. The base composition, without the antimicrobial component, can be used in industry to protect portions of surface areas from finishing processes or unwanted dyes, inks or paints. Surfaces adjacent to those which are to be finished could be coated with the surface coating composition to form a temporary barrier from the finishing substance. This protective barrier could easily be removed with water after the finishing process was completed. The base composition can also be applied to metal surfaces, such as silver, to protect such surfaces from tarnishing.

The present cream may be used not only as a barrier but as an identifier or marker for the presence of infectious bodily fluid (i.e. blood).

In some instances, it would be to a worker's advantage to be aware than small, often unnoticed or microscopic amounts of blood have, in fact, contacted their skin. This blood, or bodily fluid, if overlooked could present significant opportunity for infection. If identified as present, this blood or bodily fluid can be dealt with, thus reducing the opportunity of infection. To this objective 1% to 5% wt. tincTune of Guaiacum, Aloin, Phenolphthalin, Benzidine, or other chemicals used to detect blood (see Gaensslen Sourcebook in Forensic Serology Immunology, Nat. Inst. of Justice, pp. 101–116 (1983)) can be added to the cream. This creates an immediate change in the color of the cream in the area where a bodily fluid such as blood comes in contact with the cream containing the TincTune of Guaiacum. TincTune of Guaiacum/Guepc is a well known detector of blood used at crime scenes by forensic scientists.

The present cream may be packaged as an aerosol dispensed gel thus allowing for efficient, non-wasteful application of the product.

The cream may be packaged as an aerosol gel by combining approximately 85% cream (concentrate) and 15% propellant (i.e. propane/butane mixture, propane/isobutane mixture, fluorocarbon propellants, or singularly isobutane) using the appropriate "pressure filling" Technology (as described in *Cosmetics Science and Technology*, Edition II, Volume 2, pages 468–470 by Balsam). The same viscous characteristics of the cream make packaging this product as an aerosol gel particularly easy as they need not be cooled to a liquid state prior to insertion in the appropriate container (see "Cold Filling Techniques" *Cosmetics Science and Technology* as above). Pressurized creams/gels also offer the positive property of stabilizing the composition to the extent that a uniform increase in viscosity becomes apparent. This offers the user an increased capability to accurately meter efficient amounts of the cream thus avoiding waste.

One of the most common practiced microencapsulation in the pharmaceutical industry is to form slow-release oral dosage forms of lipophilic water-insoluble drugs. In general, water-insoluble drugs possess inherent slow-release properties, but in many cases their release rate can be increased by formulation of water-soluble drug-cyclodextrin inclusion complexes. Micro-encapsulation of such water-soluble complexes will result in drug-delivery forms with release rates independent of their water solubility. Loftsson et al., ACS Symposium Series, V520, pp. 168–189, 1993. The topical bioactive agents of the invention may be microencapsulated by these known techniques.

Microencapsulated compounds (i.e. the topical bioactive agents) may be added to the cream to react or function in specific ways in specific biological or chemical environments. This cream can also contain a series of microencapsulated compounds that serve specific functions. In these cases the cream functions not only as a barrier but as a means of delivering a specific material which has been microencapsulated and added to the cream. The cream maintains its barrier properties but also becomes a matrix or vehicle containing a bioerodible delivery device for the sustained administration of a pro-determined dosage of a drug, antimicrobial, fungicide, antiviral, antiseptic, antiflamitory, antiparasitic, insecticide, catalytic testing compounds or other compound. The encapsulation may consist of a matrix of polyvalent cation crosslinked anionic polyelectrolyte material designed to bioerode in the presence of specific chemicals or biologic environments or substances such as blood, or other bodily fluids, chemicals or specific chemical properties such as pH, conductivity, surfactant action or other chemical processes. The presence of the aforementioned substances or conditions causes the microcapsule to bioerode, releasing the internal compounds to function as designed. A drug delivery preparation with controlled release time and rate, comprising a therapeutic agent being encapsulated in or coated by a solvent membrane may be used (i.e. U.S. Pat. No. 3,965,255). The process of microencapsulation per se is well known in the art (i.e. U.S. Pat. Nos. 3,962,414 and 5,517,982).

The phrase "consisting essentially of" as used herein covers combinations with some additional elements but excludes additional unspecified ingredients which would affect the basic and novel characteristics of the product defined in the balance of the claim. In other words, the phrase "consisting essentially of" excludes ingredients that would materially affect the basic and novel characteristics of the claimed composition. The phrase "consisting essentially of" does not exclude the addition of another ingredient which does not materially affect the characteristics of the invention.

The topical barrier creams of the invention are formulated and prepared by mixing alkali metal silicate (i.e. sodium silicate solution or sodium metasilicate) with a polyol effective as an emollient, such as glycerol, an alkali-metal fatty acid salt having from 8 to 18 carbon atoms, such as sodium laurate, water (i.e. distilled water) and a topical bioactive agent such as an antimicrobial. The mixture is then heated to 70° C. until the mixture changes to a semi-viscous liquid.

The following non-limiting examples illustrate the invention:

EXAMPLE 1

An antimicrobial cream having the following composition of ingredients is prepared:

Nonoxynol-9 4 wt. %
Sodium laurate 25 wt. %
Sodium silicate 1 wt. %
Glycerin 14 wt. %
Purified water Balance These ingredients are heated to approximately 70° C., then stirred until cool. The resulting cream is then stored in a tube or other conventional container for later use.

The foregoing composition is applied to a small open wound and observed to collect there, effectively filling in the wound. This additional protection for open wounds or sores, in combination with the low toxicity of the cream, is particularly effective for purposes of the invention.

EXAMPLE 2

This Example shows that the preparation of the invention will function as a barrier to the passage of infectious agents and perhaps toxic or irritating substances.

The following composition is used:

Sodium laurate 25 wt. %
Sodium silicate 1 wt.
Glycerin 14 wt. %
Purified water Balance Radiolabeled Virus—Vero (African Green Monkey Kidney) cells, grown using standard procedures, are used for preparation of labeled viral stocks. The cells are infected with HSV-1 strain KOS at a multiplicity of 2 pfu/cell. Five hours post-infection $^3$[5]-methionine is added to the media (40 µCi/ml final concentration) and the cells are incubated at 37° C. When 90–100% of the cells show evidence of infection, they are scraped from the plate and collected by centrifugation at 500 xg for 10 minutes. Radiolabeled virions are then isolated as described by Visalli et al., *Virus Res* 29, 167–178 (1993). Briefly, the cells, suspended in RSB buffer, are frozen and thawed 3 times to release virus and centrifuged at 500 xg for 10 minutes to remove the debris. The supernatant containing virus is layered on a cushion of 36% sucrose in RSB and centrifuged at 13,000 rpm for 80 minutes in a Beckman SW28 rotor to pellet the virions. The pellet is resuspended in RSB and the cushion centrifugation step is repeated. The pellet is resuspended in RSB and the radioactivity determined.

Barrier Assay—A modification of the method of Oz et al., *Infect Cont Hosoital Epidem* 12, 93–95 (1991). Briefly, Whatman filter paper (qualitative #2) is cut into small sections. One filter section is coated with the cream and a second control filter paper section is wetted and blotted to dampness. The filter containing the cream is weighed to determine the amount of cream used. Both filter papers are placed on dry filter paper sections to form 2 layers. The radiolabeled virus suspension (100 µl, 5×10$^4$ cpm, in RSB) is then placed on the top filter paper and at various times (0, 5, 15, 30, 60, and 180 minutes) the top filters are removed. The bottom filters are then placed in scintillation fluid (Redisolve HP, Beckman Instruments) and the amount of label passing through the top filters determined in a Beckman LS2801 scintillation counter. All samples are done in duplicate and average values are reported.

Figure 2:
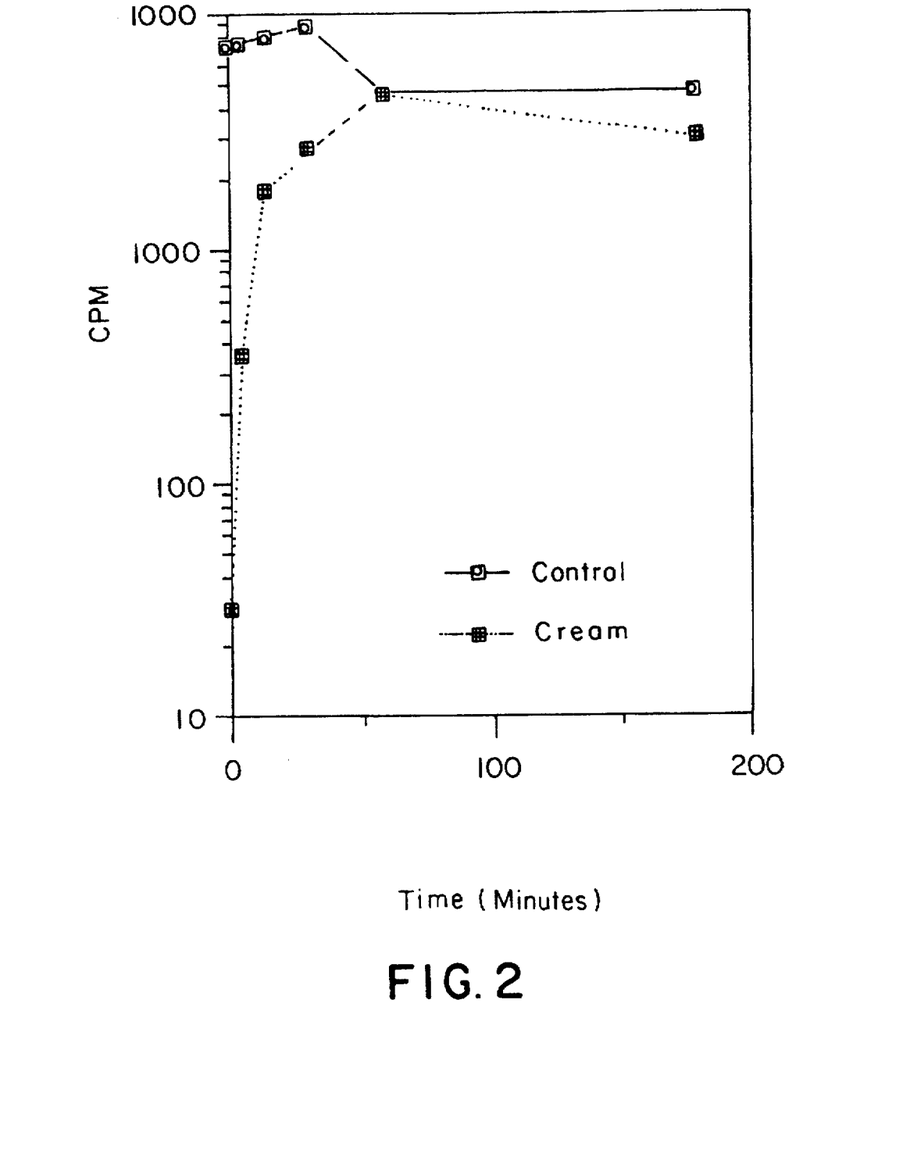
FIG. 2 shows how much radiolabeled virus passes through a filter coated with the composition of the invention with the passage of time.

Weighing of the filters before and after application of the cream reveal an average of 0.12±0.04 g of cream. Radiolabeled virus passes immediately through the control filter (FIG. 2). Saturation (approximately 7,000 cpm per filter) is reached as soon as we could measure the transfer. In contrast, the cream reduced the rate of transfer of radiolabeled virus. At time 0, only 29 cpm transfers to the bottom filter. Increasing amounts of label transferred through the barrier, but saturation is not reached until 60 minutes. Transfer through the cream occurs with first order kinetics.

When the control values are set at 100% (FIG. 1) and the data is plotted as a percent of the control, only 0.4% of the virus had passed through at time 0. At 5 minutes, only 4.5% had passed and this increased slowly until 60' when 96.5% had transferred.

Figure 1:
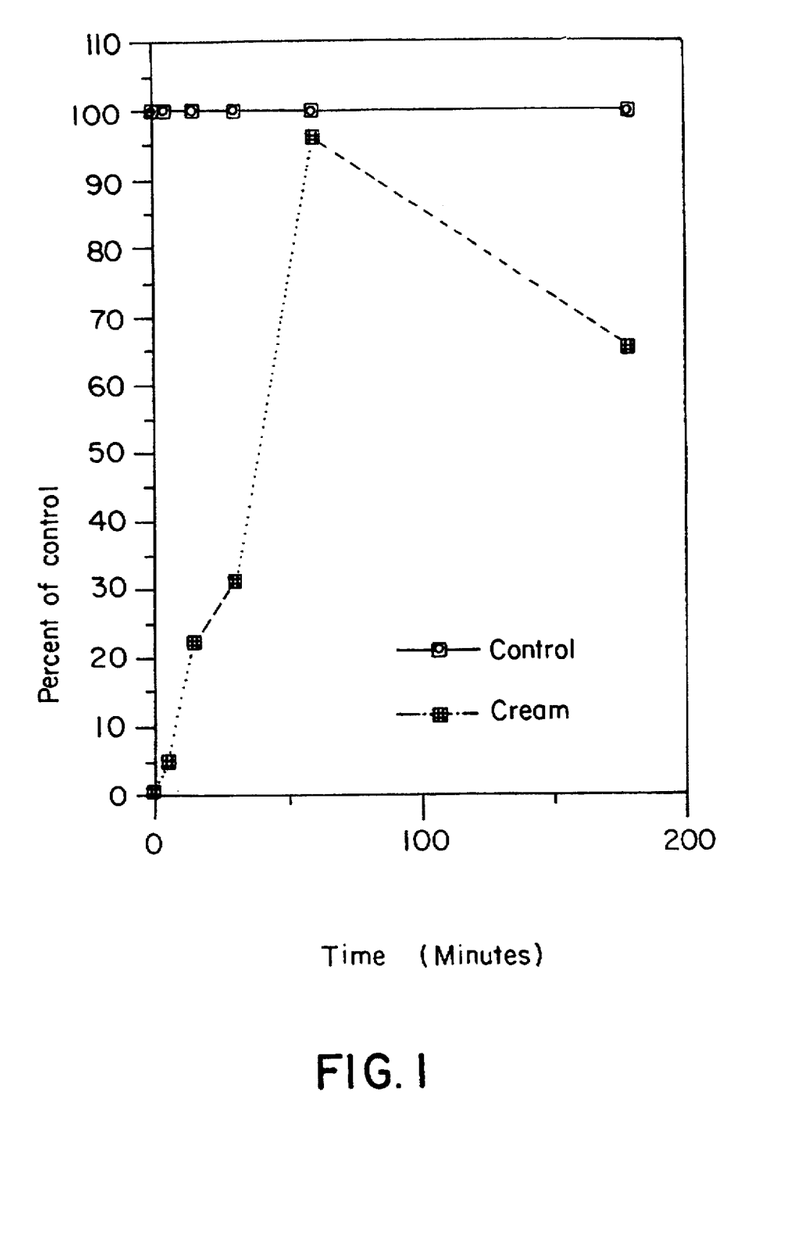
FIG. 1 shows data plotted as a percent of the control and demonstrates how much virus passes through the composition of the invention with the passage of time.

These results demonstrate that the cream has barrier activity. The presence of the cream delays passage of the label by up to 60 minutes. The differences at times up to 30 minutes are significantly different, indicating a substantial barrier effect is obtained. These results compare favorably with those of others (e.g., Oz et al., *Infect Cont Hospital Epidem* 12, 93–95 (1991)) who use a lanolin-based gel.

EXAMPLE 3

Nine anti-bacterial solutions are formulated which contain either aqueous sodium metasilicate or sodium silicate solution. The first five solutions are prepared by varying sodium metasilicate from 1–5 weight percent. The final four are prepared with the sodium silicate solution in weight percents of 1.8, 3.6, 5, and 9.5. In addition to these silicate compounds, each solution contain glycerol (14 wt. %), sodium laurate (25%), Nonoxynol-9 (4%), and the remainder Milli-Q distilled water. The initial mixture is a white, fluffy powder that contains about 80% sodium laurate by volume. The mixture is heated to 70° C. and the powder turns to a clear, viscous liquid. After cooling to room temperature, the end product is a, white semiviscous cream. The pH of the products are about 10.

The nine solutions are changed by varying the weight percent of the two silicate compounds. Table 2 shows the actual component weights and weight percents for the first set of runs. Weights and weight percents for the second set of runs are shown in Table 3.

The next step is to analyze each component for its potential hazards, general uses, physical properties, and related names. Shown below is a summary for each of the components, excluding distilled water.

Sodium Metasilicate

In general, the use of silicates in coatings and adhesives in contact with foods and small amounts of liquid silicates are accepted by the FDA and are regularly used to prevent corrosion in canned drinking water. On the other hand, silicates need to be handled properly due to their moderately to strongly alkaline pH (pH 10–12) and buffering properties. As a result of the basic nature of sodium silicate, many applications have been recognized including: detergents, "builders" for bar soaps, films, coatings, and concrete treatment. In detergents the sodium silicate acts as a deflocullator (breaking particulate particles into fine particles which stay suspended in solution) and a buffer (resisting pH changes). Also, an important property of sodium silicate, shown in concrete treatment, is the ability to act as a sealant. Thus, it forms an insoluble gel within the concrete pores providing protection from water, oil, and acid. The physical properties

TABLE 2

Sodium Metasilicate Solution Data

| Component | Trial 1 (solution SP-1) | | Trial 2 (solution SP-2) | | Trial 3 (solution SP-3) | | Trial 4 (solution SP-4) | | Trial 5 (solution SP-5) | |
|---|---|---|---|---|---|---|---|---|---|---|
| | Mass (g) | Weight % | Mass (g) | Weight % | Mass (g) | Weight % | Mass (g) | Weight % | Mass (g) | Weight % |
| sodium laurate | 7.50 | 24.93 | 7.50 | 24.83 | 7.50 | 24.79 | 7.49 | 24.86 | 7.50 | 24.93 |
| sodium metasilicate *5H2O | 0.52 | 1.73 | 1.03 | 3.41 | 1.56 | 5.16 | 2.09 | 6.94 | 2.63 | 8.74 |
| glycerol | 4.24 | 14.10 | 4.19 | 13.87 | 4.22 | 13.95 | 4.21 | 13.97 | 4.21 | 13.99 |
| Nonoxynol-9 | 1.22 | 4.06 | 1.29 | 4.27 | 1.23 | 4.06 | 1.24 | 4.12 | 1.26 | 4.19 |
| Milli-Q | 16.60 | 55.19 | 16.20 | 53.62 | 15.75 | 52.05 | 15.10 | 50.12 | 14.49 | 48.16 |
| Total | 30.08 | 100.00 | 30.21 | 100.00 | 30.26 | 100.00 | 30.13 | 100.00 | 30.09 | 100.00 |

TABLE 3

Sodium Silicate Solution Data

| Component | Trial 1 (solution SS-1) | | Trial 2 (solution SS-2) | | Trial 3 (solution SS-3) | | Trial 4 (solution SS-4) | |
|---|---|---|---|---|---|---|---|---|
| | Mass (g) | Weight % | Mass (g) | Weight % | Mass (g) | Weight % | Mass (g) | Weight % |
| sodium laurate | 7.50 | 24.93 | 7.49 | 24.79 | 7.53 | 24.88 | 7.51 | 24.93 |
| sodium silicate solution | 0.55 | 1.83 | 1.08 | 3.57 | 1.51 | 4.99 | 2.84 | 9.43 |
| glycerol | 4.18 | 13.90 | 4.22 | 13.97 | 4.24 | 14.01 | 4.19 | 13.91 |
| Nonoxynol-9 | 1.19 | 3.96 | 1.19 | 3.94 | 1.29 | 4.26 | 1.21 | 4.02 |
| Milli-Q | 16.57 | 55.09 | 16.25 | 53.79 | 15.47 | 51.12 | 14.23 | 47.23 |
| Total | 29.99 | 100.00 | 30.23 | 100.00 | 30.04 | 100.00 | 29.98 | 100.00 |

The system analyzed is classified into one of four categories which includes: suspensions, emulsions, lotions, and ointments.

Suspensions: Dispersions of solid particles in a liquid continuous phase with or without the aid of a suspending agent. It may be used for oral or external use.

Emulsions: Dispersion of two immiscible liquids. One liquid is dispersed as small globules in the other liquid with the aid of an emulsifying agent.

Lotions: Liquids that are intended for topical or external application to the skin. In some cases, they contain suspended solid particles.

*Ointments: Semi-solid preparations intended for application to the skin. They may consist of oleaginous substances, may be free from oleaginous substances, and/or be classified as emulsions.

of solid sodium metasilicate include: small off white solid particles, density of about 1.7 g/ml, melting point about 70° C., high water solubility. Some of the related names for this compound are Disodium Monosilicate and Metso beads 2048.

Nonoxynol-9

This component is fairly harmless when weight percentages of 0 to about 15% are used in solution. For over 30 years nonoxynol-9 (i.e. N-9) has been used as a spermicide in many over the counter contraceptive products. Another important use is for protection against viruses. When used in spermicide at 5% concentrations, N-9 has the capability to inactivate many sexually transmitted pathogens primarily by their detergent affect on bacteria cell membranes and viral envelopes. Also, N-9 can be used between standard latex gloves to improve surgical glove safety compared with latex gloves alone with respect to needlestick transmission of the virus, HIV-1. The physical properties of N-9 include: light yellow to colorless liquid, density of about 1.06 g/ml, viscosity of about 175 to 250 cp., high water solubility. Another name for nonoxynol-9 is Triton N-101.

Glycerol

Since 1959 glycerol has been recognized and safe as a general food additive and has been safely tested intravenously in concentrations of less than 5%. Several uses for glycerol which include food additives (syrup), drugs, and cosmetics all incorporate the ability of glycerol as a solvent, a moistening agent, or a lubricant. For example, it is used in toothpaste to maintain the desired smoothness and viscosity. Also, glycerol is used in many creams and lotions to keep the skin soft and replace skin moisture. The physical properties of glycerol include: light brown liquid, density of about 1.47 g/ml, viscosity 1499 cp., melting point of about 18.2° C., and high solubility in water and alcohol (not hydrocarbons). Glycerin, propane-1,2,3-triol are other synonyms for glycerol.

Sodium Laurate

This component is an extremely low dense white powder is soluble in water.

The final step after defining the system and analyzing each component is to design suitable preparation criteria. The primary objectives for formulation are: any solid particles of the suspended drug should be of a relatively uniform size so they act uniformly, particle sizes should be such that in the case of topically applied suspension is not gritty when applied, and insure a minimum of aggregation and flocculation. The general method for compounding is shown below step by step.

1. Reduce large solid particles in a mortar.
2. Solids are wetted with aqueous components such as glycerin.
3. Once a smooth paste has been formed, bring to final volume with final aqueous components.
4. Heat to appropriate temperature at a constant rate until complete solubility is attained and let cool to final form.

Finally, steps could be taken to increase or decrease the viscosity or "liquid" like property in the final prepared solution. Mainly glycerol or possibly water can be added to decrease the viscosity to more of a gelatin type product. If the product proves to be non-viscous, sodium laurate or silicate can be added.

The procedure for preparing an ointment containing glycerol (14 wt %), sodium laurate (25%), Nonoxynol-9 (4%), sodium metasilicate (1%) and the remainder distilled water is as follows.

Equipment
 Analytical balance
 Hot plate with magnetic stirrer
Materials
 Glycerol (Aldrich, catalog #56-81-5, lot #12131KZ)
 Nonoxynol-9 (Aldrich, catalog #26027-38-3, lot #04510JX)
 Milli-Q distilled water
 Sodium laurate (Sigma, catalog #629-25-4, lot #62H5003)
 Sodium metasilicate pentahydrate (Sigma, cat. #10213-79-31, lot #92H2624)
 Sodium silicate solution (Aldrich, catalog #1344-09-8, lot #17703BZ)
Preparation 1) Add 7.5 g of sodium laurate to a 100 ml beaker, followed by 0.52 g of sodium metasilicate, 4.2 g of glycerol, and 1.2 g of Nonoxynol-9.

2) Fill with distilled water until a total solution weight of 30 g is obtained. The solution level will drop so the walls of the beaker were rinsed while adding the distilled water. A white fluffy solid should result that fills approximately half the beaker (about 50 ml).

3) Heat solution up to 70° C. in a hot water bath with a magnetic stirrer. The solution should turn to a clear, viscous liquid with a yellow tint.

4) Remove solution from the hot water bath and cool at room temperature. As the solution approaches room temperature, a white precipitate should be observed.

Two anti-bacterial ointments are formulated with identical components except one contained sodium metasilicate (solution 1) and the other sodium silicate solution (solution 2). Solution 1 is prepared by varying the weight % of sodium metasilicate from 1–5% in increments of 1%. Solution 2 is prepared by using 1.8 wt %, 3.6%, 5%, and 9.5% of sodium silicate solution.

Before the solutions are heated, both are a fluffy, white solid with sodium laurate occupying about 80% of the volume. Solution 1 has a greater volume because the sodium laurate is slightly dissolved. After heating, the solutions are a clear, viscous liquid with a yellow tint.

Once the solutions are cooled to room temperature, a white solid forms that has properties similar to a bar of soap. Solution 1 solidifies from the top and bottom, while solution 2 precipitates from the top. Solution 1 solidifies faster than solution 2, approximately 15 minutes compared to 25 minutes. Trials SS-2 and SS-3 of solution 2 never fully solidify, so they are mixed by poking holes through the top layer with a stirring rod. A clear gel is found under the precipitate in SS-2 and a clear liquid found under the SS-3 precipitate. After mixing, the two solutions are uniform with trial SS-2 softer than the other trials.

EXAMPLE 4

This example evaluates (i) the in vitro effectiveness of the formulation as a barrier to the passage of virus, and (ii) determines if the formulation has a direct virucidal effect.

The basic strategy for evaluating the barrier function of the formulation will be to coat a porous surface with the formulation, place a solution containing the virus on one side, and then measure the amount of virus that passes through the barrier.

The function as a barrier may depend on cell/organism size. Therefore, a small mouse picornavirus called GDVII (27 nm diameter) and a relatively large virus HSV-1 (150 to 200 nm diameter) will be tested.

The function of the barrier may depend on whether the virus has an envelope. The use of GDVII and HSV-1 will confirm this possibility since the former lacks an envelope and the latter is enveloped.

Initial experiments use viruses radioactively labeled by known techniques and purified before use to remove interfering cellular debris. The radioactively labeled virus will provide a very sensitive assay for penetration.

Although some radiolabeled virus may pass the barrier, this virus should be rendered non-infectious by an antimicrobial such as nonoxynol-9. Therefore the fluid on the opposite side of the barrier will be tested for infectious viruses using a plaque assay or serial dilution assay on appropriate cell lines.

Nonoxynol-9 (1–3%) will also be used in the barrier in some tests to determine if the effectiveness can be increased.

Vero cells, which are used for HSV-1, will be grown in DME with 5% serum as described previously (Grau et al., 1989; Brandt and Grau, *Invest Ophthalmol Vis. Sci.* 31, 2214–2223, 1990; Brandt et al., *J. Virol. Meth.* 35: 127–135, 1991; Visalli and Brandt, *Virology* 185: 419–423, 1991; Brandt et al., *Ophthalmic Research*, 1992. Mouse L-929 cells, for growth of GDVII virus, will be grown in the same media. High titer stocks of HSV-1 strain KOS will be grown as described in Grave et al., 1989. High titer stocks of GDVII virus will be grown as described in previously (Brandt and Salkowski, *Invest. Ophthalmol Vis. Sci.* 33: 113–120, 1992. Plaque assays will be carried out using 2% methocell overlay by conventional techniques.

Virus will be radiolabeled using [$^{35}$S]-methionine (40 µg/ml) as described previously (Visalli and Brandt, *Virology*, 185: 419–423, 1991; Viruses will be purified using sucrose gradients as described previously.

To assay for barrier function, we will use double well plates (Falcon #3090, 3091, 3095, or 3096). These plates contain an insert with a porous membrane (0.45 or 3 µm) at the bottom. Membranes of both pore sizes will be used. The membrane on the insert will be coated with the barrier and inserted into the well of the culture plate. The well in the culture plate will contain media in contact with the underside of the membrane. The virus suspension ($1\times10^6$ cpm) will then be added to the insert and at various times (0, 15', 30', 60', 3 hr, 6 hr, 24 hr, and 48 hr). The media in the well will be removed and then assay for the presence of radiolabeled virus by scintillation counting or infectious virus by plaque assay. To ascertain the effect of drying on the barrier, the barrier function will be tested immediately after application and after drying for 30 and 60 min prior to the addition of the virus. This or a modification of the method of Oz et al., *Infect. Cont. Hospital Epidem.* 12, 93–95 (1991), which is the method used for example 2, may be used.

As a control to test whether the barrier is formed, a solution containing $^3$H-labeled water will be placed in the insert and penetration of the label will be measured. The use of $^3$H for this test will not interfere with the viral penetration assay since the viruses will be labeled with [$^{35}$S]-methionine. After determining that the barrier was established, the $^3$H solution will be removed and the virus suspension will be added.

The formulation will be applied to the membrane of the insert using a cotton or dacron tipped swab.

In order to evaluate virucidal activity, the barrier cream, with or without nonoxynol-9, will be applied to the bottom of a cell culture well (Falcon #3047 24 well plate). A solution of infectious virus will then be added and incubated at 37° C. At various times (see above) the amount of surviving virus will be measured by plaque assay on appropriate cells. As a control, virus will be added to untreated tissue culture wells. Between 10$^3$ and 10$^6$ plaque forming units (pfu) will be used initially. If no effect is observed, 1×10$^2$ pfu will be tested.

EXAMPLE 5

This example tests in vitro the barrier and antimicrobial activity of the cream. Previous examples showed the barrier effect of the cream per se. In this example, the properties of the antimicrobial will be assayed to eliminate the different viruses that are in contact with the cream.

The formulation of the cream is as follows:

Nonoxynol-9 4 wt. %

Sodium laurate 25 wt. %

Sodium silicate 1 wt. %

Glycerin 14 wt. %

Purified water Balance

The amounts of antimicrobials is then varied. The first to be tested will be non-oxynonol-9 at a range of 0.01 to 15 wt %.

The HSV (herpes simplex virus) viruses will be labeled and incubated. When 90–100% of the cells show evidence of infection they will be collected. The methods of growing and collection of the viruses will be the same as described in previous Examples.

The FDA considers nonoxynol-9 to be safe and effective. Laboratory studies indicate that nonoxynol-9, a nonionic surfactant used as a spermicide, inactivates HIV and other sexually transmitted pathogens. Evidence from in vitro studies suggests that spermicides containing nonoxynol-9 may be effective in preventing the transmission of HIV (Lancet March 19, p. 654, 1987). In assay studies, formulations containing amounts of the spermicide was found to inactivate HIV at concentrations of between 0.1 to 1.0% and nonoxynol-9 alone was active at 0.05%. Using the methods of the previous Examples the cream with nonoxynol-9 at levels from 0.1 to 15% wt will be tested. Briefly white filter paper is cut into small sections. One filter section coated with the cream and a second control filter paper is wetted and blotted to dampness. Cream will be weighed, and both filter papers placed on dry filter paper sections to form 2 layers. The virus (radiolabled) placed on top of filters. The bottom filters will then be placed in scintillation fluid and the amount of label passing through the top filter determined in a scintillation counter. Studies to determine the efficacy of the antimicrobial compound have used rabbit models. At this point, the eyes of the rabbits will be infected to detect if the HSV virus, the leading cause of blindness due to infectious diseases in developed countries, will cloud the eye if still active. Another method is a new murine model of herpes simplex virus-induced ocular disease for antiviral drug testing (Brandt, et al. *Journal of Virological Methods*, 36 (1992)). Other active ingredients can be similarly tested. Such active ingredients include:

Fungicides, soaps, antibiotics, antiviral, anti-infectives, insect repellents and athletes foot medications.

Microencapsulating of all of the above will be performed by known techniques described previously.

Aerosol applications and adding color by known methods for alerting the wearer to the presence of bodily fluids will be performed.

It will be understood that the foregoing description is of preferred exemplary embodiments of the invention, and than the invention is not limited to the specific forms shown. Modifications may be made in the design and arrangement of the elements without departing from the scope of the invention as expressed in the appended claims.

We claim:

1. A protective skin cream composition consisting essentially of:

(i) 15 to 40 wt. % of an alkali-metal fatty acid salt having from 8 to 18 carbon atoms, (ii) an effective amount of an antimicrobial compound, (iii) 5 to 20 wt. % of a polyol effective as an emollient, (iv) 0.5 to 8.0 wt. % of an alkali metal silicate, and (v) the balance water, said composition being removable with soap and water;

wherein the antimicrobial compound is effective against viruses.

2. The composition of claim 1, wherein the cream is in the form of an oil-in-water emulsion.

3. The composition of claim 1, wherein the polyol is selected from the group consisting of glycerin, sorbitol and propylene glycol, and the alkali metal silicate is sodium or potassium silicate.

4. The composition of claim 1, wherein the antimicrobial compound is AZT or nonylphenoxy-polyethoxyethanol.

5. A method of protecting a person from infection from bodily fluids, which comprises:
   (1) applying to the skin of said person a protective skin cream composition of claim 1, which composition dries to form a film on the skin effective as a topical barrier against bodily fluids, the film containing the antimicrobial compound in an amount effective to kill one or more types of microbial organisms, and the film being removable with soap and water;
   (2) wearing the film while performing a task in close proximity to said bodily fluids; and
   (3) removing the film from said person's skin upon completion of a task with soap and water.

6. The method of claim 5, wherein the task comprises a surgical operation or procedure on a patient having blood.

7. The method of claim 6, wherein the blood of the patient is contaminated with HIV.

8. The method of claim 6, wherein the surgical operation or procedure involves contact between the blood of the patient and a worker performing said task.

9. The method of claim 6, further comprising a step of putting on a protective garment over skin to which the protective composition has been applied.

10. The method of claim 6, further comprising the steps of putting on protective garments, and applying the protective composition to exposed areas of skin.

11. The method of claim 9, further comprising applying the protective composition to the face of a worker.

12. The method of claim 5, further comprising performing steps (1) to (3) two or more times during the same day.

13. A protective skin cream composition consisting essentially of:
   (i) 15 to 40 wt. % of an alkali-metal fatty acid salt having from 8 to 18 carbon atoms,
   (ii) an effective amount of topical bioactive agent,
   (iii) 5 to 20 wt. % of a polyol effective as an emollient,
   (iv) 0.5 to 8.0 wt. % of an alkali metal silicate, and
   (v) the balance water, said composition being removable with soap and water.

14. A method of protecting a person which comprises:
   (1) applying to the skin of said person a protective skin cream composition of claim 13, which composition dries to form a film on the skin effective as a topical barrier, the film containing the topical bioactive agent and the film being removable with soap and water;
   (2) wearing the film; and
   (3) removing the film from said person's skin with soap and water.

15. A protective skin cream composition consisting essentially of:
   (i) 15 to 40 wt. % of an alkali-metal fatty acid salt having from 8 to 18 carbon atoms,
   (ii) 5 to 20 wt. % of a polyol effective as an emollient,
   (iii) 0.5 to 8.0 wt. % of an alkali metal silicate, and
   (iv) the balance water, said composition being removable with soap and water.

16. A method of protecting a person which comprises:
   (1) applying to the skin of said person a protective skin cream composition of claim 15, which composition dries to form a film on the skin effective as a topical barrier, and the film being removable with soap and water;
   (2) wearing the film; and
   (3) removing the film from said person's skin with soap and water.

17. The composition of claim 13, wherein an effective amount of a detecting agent for determining that a body fluid is present is added.

18. The composition of claim 13, wherein said composition is an aerosol dispensed gel.

19. The composition of claim 13, wherein said topical agent is microencapsulated.

20. The composition of claim 15, wherein said composition delays the passage of radio labeled virus by up to 30 minutes.

21. The composition of claim 15 wherein said composition delays the passage of radio labeled virus by up to 20 minutes.

* * * * *